United States Patent [19]

Rawlings et al.

[11] Patent Number: 5,665,366
[45] Date of Patent: Sep. 9, 1997

[54] SKIN CARE METHOD AND COMPOSITION

[75] Inventors: Anthony Vincent Rawlings, Wyckoff, N.J.; Allan Watkinson, Bedford, Great Britain

[73] Assignee: Elizabeth Arden Co., Division of Conopco, Inc., New York, N.Y.

[21] Appl. No.: 582,033

[22] Filed: Jan. 2, 1996

Related U.S. Application Data

[63] Continuation of Ser. No. 304,718, Sep. 12, 1994, abandoned.

[30] Foreign Application Priority Data

Sep. 15, 1993 [GB] United Kingdom .................. 9319103
Mar. 22, 1994 [GB] United Kingdom .................. 9405639

[51] Int. Cl.$^6$ ........................................................ A61K 7/00
[52] U.S. Cl. ........................ 424/401; 424/195.1; 514/844; 514/859
[58] Field of Search ........................ 424/401, 195.1; 514/844–848, 859

[56] References Cited

U.S. PATENT DOCUMENTS

| | | | |
|---|---|---|---|
| 4,715,899 | 12/1987 | Chanda et al. | 134/26 |
| 4,784,854 | 11/1988 | Seguin | 424/401 |
| 5,053,230 | 10/1991 | Gazzani | 424/582 |
| 5,130,142 | 7/1992 | Wong | 424/574 |
| 5,230,891 | 7/1993 | Nakayama | 424/401 |
| 5,384,126 | 1/1995 | Bonte | 424/450 |

FOREIGN PATENT DOCUMENTS

| | | |
|---|---|---|
| 0141405 | 11/1980 | Japan . |
| 0 365 004 | 1/1932 | United Kingdom . |
| 1 543 391 | 4/1979 | United Kingdom . |
| 2 178 312 | 2/1987 | United Kingdom . |
| 84/02846 | 8/1984 | WIPO . |
| 93/19732 | 10/1993 | WIPO . |

OTHER PUBLICATIONS

Lundström, A. et al., "Cell Sheeding from Human Plantar Skin in Vitro: Evidence of its Dependence on Endogenous Proteolysis", *The Society for Investigative Dermatology, Inc.*, vol. 91, (1988), pp. 340–343.

Lundström, A. et al., "Cell Sheeding from Human Plantar Skin In Vitro: Evidence that Two Different Typoes of Protein Structures are Degraded", *Arch. Dermatol. Res.*, (1990), vol. 282, pp. 234–237.

Lundström, A. et al., "Evidence that Cell Sheeding from Plantar Stratum Corneum in Vitro Involves Endogenous Proteolysis of the Desmosomal Protein Desmoglein I", *The Society for Investigative Dermatology, Inc.*, (1990), vol. 94, pp. 216–220.

Egelrud, Torbjörn, "Stratum Corneum Chymotryptic Enzyme: Evidence of its Location in the Stratum Corneum Extracellular Space", *European Journal of Dermatology*, (1992), vol. 2, pp. 46–49.

Lundström, A. et al., "Stratum Corneym Chymotryptic Enzyme: A Proteinase Which may be Generally Present in the Stratum Corneum and with a Possible Involvement in Desquamation", *Acta Dermato. Vernesol.*, (1991), vol. 71, pp. 471–474.

Horie et al., "Detection and Characterisation of Epidermal Proteinases by Polyacrylamide Gel Electrophoresis", *Comp. Biochem. Physiol*, 77B, (1984), pp. 349–353.

Resing, Katheryn et al., "Structure and Function of Epidermal Proteases and Their Inhibitors", *The Biological Role of Proteinases and their Inhibitors in Skin*, New York, (1986), pp. 39–38.

(List continued on next page.)

*Primary Examiner*—Gollamudi S. Kishore
*Attorney, Agent, or Firm*—Rimma Mitelman

[57] ABSTRACT

A composition for topical application to the skin for alleviation or prevention of dry flaky skin conditions, dandruff or ache comprising one or more stratum corneum trypsin-like enzymes. The composition may further comprise an additional enzyme selected from glycosidases, other proteases, lipases and mixtures thereof. Optional additional active ingredients include sunscreens, lipids, hydroxy carboxylic acids and ketocarboxylic acids.

7 Claims, 4 Drawing Sheets

Effect on stratum corneum desmocollin 1 degradation

OTHER PUBLICATIONS

Hopsu–Havu, V. K. et al., "Localization of Cathepsins H and L and Their Inhibitors in Stratified Epithelia and Lumphatic Tissue", *The Biological Role of Proteinases and their Inhibitors in Skin*, New York, (1986), pp. 27–37.

Etherington, D. J. et al., "The Role of Collagen–Degrading Cysteine Proteinases in Connective Tissue Metabolism", *Cysteine Proteinases and Their Inhibitors*, Proceedings of the International Symposium, Portorox, Yugoslavia, Sep. 15–18, 1985, New York (1986), pp. 269–282.

Harvima, Rauno J. et al., "Separation and Identification of Cathepsins in Newborn Rat Epidermis", *The Society for Investigative Dermatology, Inc.*, (1987) vol. 88, No. 4, pp. 393–397.

Ando, Yoshihiro et al., "Purification and Characterization of Calpains from Pig Epidermis and Their Action on Epidermal Keratin" *The Society for Investigative Dermatology, Inc.*, (1988) vol. 90, No. 1, pp. 26–30.

Fräki, Jorma E., "Human Skin Proteases: Effect of Separated Proteases on Vascular Permeability and Leukocyte Emigration in Skin", *Acta Dermatovener* (Stockholm) vol. 57, (1977), pp. 393–398.

Heikkinen, J. E., et al., "Purification and Biochemical Characterization of Rat Skin Cathepsin D", *The Journal of Investigative Dermatology*, vol. 65, No. 3, Sep. 1975, pp. 272–278.

Stratum corneum trypsin-like enzyme: Superose 12 fractionation

SKIN CARE METHOD AND COMPOSITION

This is a continuation of application Ser. No. 08/304,718, filed Sep. 12, 1994, now abandoned.

The present invention relates to compositions for topical application to the skin and their cosmetic and pharmaceutical use. In particular, the invention relates to compositions comprising stratum corneum trypsin-like enzymes and their use in alleviating or preventing conditions involving abnormal desquamation by facilitating desmosomal degradation.

In normal, healthy epidermis the continuous production of new stratum corneum is balanced by a well-regulated shedding of corneocytes from the skin surface. Little is known about this desquamation process at the molecular level.

It has been shown by A. Lundström and T. Egelrud (J. Invest Dermatol, (1988) 91 340–343; Arch Dermatol Res (1990) 282 234–237; J. Invest Dermatol (1990) 94 216–220) that cohesion between cells in the stratum corneum is dependant on protein structures. These structures must be degraded before cell dissociation can occur.

Furthermore, evidence has been provided to show that cell dissociation is preceded by a degradation of the extracellular parts of desmosomes (T. Egelrud (1992) European Journal of Dermatology 2 46–49).

It is thought that the process of desquamation involves proteolytic degradation of desmosomes, causing the cohesive links between the cells to break down and thereby allowing detachment of peripheral corneocytes from the surface of the stratum corneum.

Little is known about the proteases thought to be involved in the desquamatory process. One particular protease, the serine protease stratum corneum chymotryptic-like enzyme (SCCE) has been implicated as a putative desmosomal degrading enzyme (see A. Lündstrom and T. Egelrud, Acta Derm Venersol (Stockh) (1991) 71, 471–474).

The present inventors have now found that the stratum corneum additionally contains serine proteases having trypsin-like substrate specificity, hereinafter referred to as stratum corneum trypsin-like enzymes (SCTE), which may be involved in the process of cell dissociation (desquamation) and desmosomal degradation. These enzymes are therefore of interest in the treatment of conditions where the underlying aetiology indicates that assisting the processes of desmosomal degradation and/or desquamation would be beneficial.

Accordingly the invention provides a composition for topical application to the skin, comprising one or more stratum corneum trypsin-like enzymes.

Figure 1:
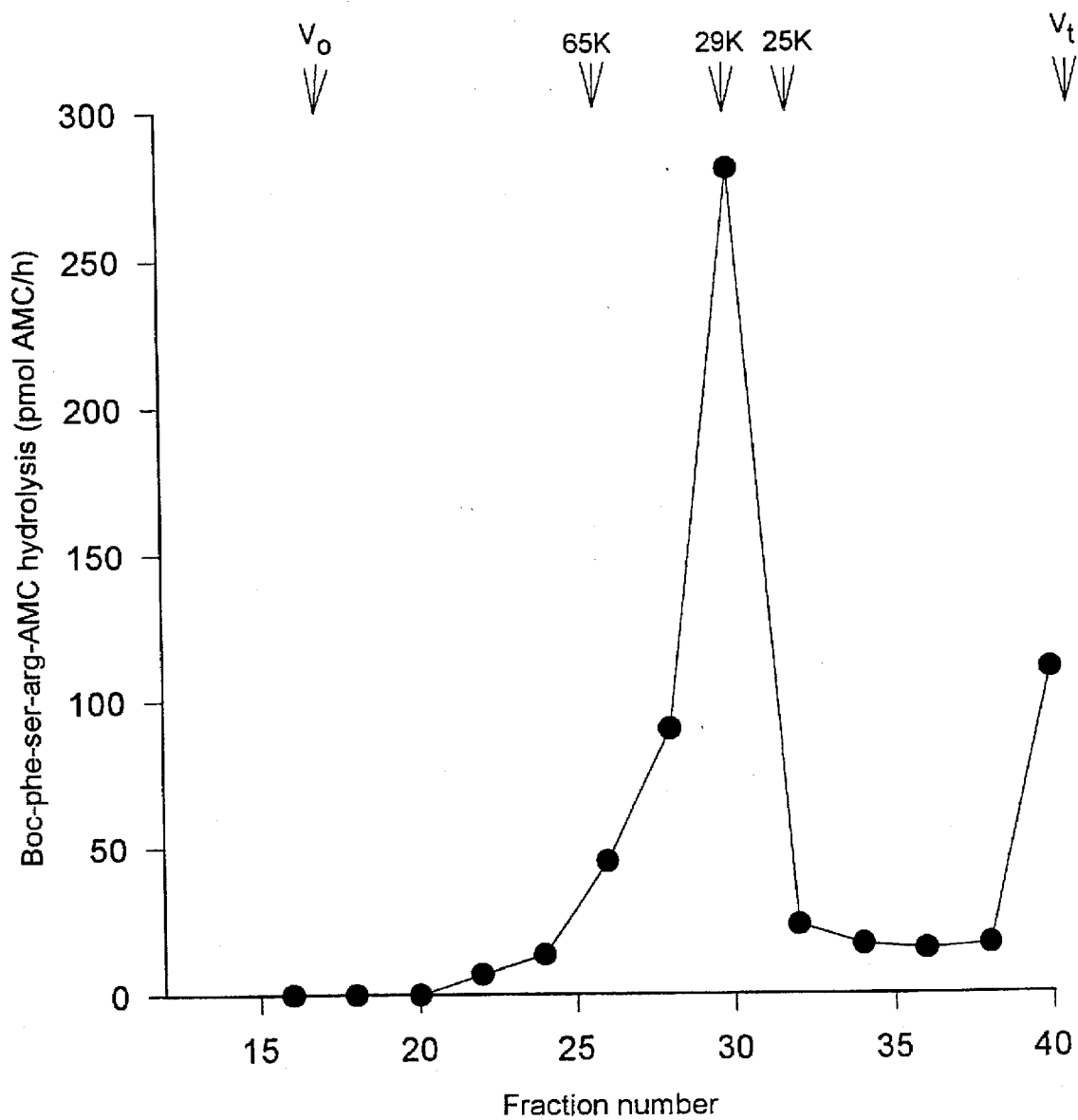
FIG. 1 depicts fractionation profile of stratum corneum extract.

As used herein, the term "stratum corneum trypsin-like enzyme" means a stratum corneum serine protease, or a pro-enzyme thereof, which in its active form exhibits similar substrate sensitivity and inhibitor sensitivity to trypsin. More specifically, the term "stratum corneum trypsin-like enzyme" means a serine protease, or a pro-enzyme thereof, which in its active form is inhibited by antipain, and leupeptin. More particularly, the term "stratum corneum trypsin-like enzyme" means an enzyme which in its active form is capable of decomposing the substrate boc-phe-ser-arg-aminomethylcoumarin (AMC).

It will be appreciated that a pro-enzyme is an inactive form of the enzyme which may be activated by appropriate proteolytic cleavage to give the active form.

Suitable stratum corneum trypsin-like enzymes for use according to the present invention have apparent molecular weights, as determined by the method of comparing the electrophoretic mobility with standard proteins on sodium dodecyl sulphate polyacrylamide gel electrophoresis of 24 kDa, 26 kDa and 27 kDa.

Preferably the composition comprises 0.00001 to 50% more preferably 0.001 to 20% and even more preferably 0.001 to 0.1% by weight of the composition stratum corneum protease enzyme.

Stratum corneum trypsin-like enzymes may be extracted from human or animal skin or callus by high salt solution (e.g. 1M NaCl), detergent or solvent extraction, and purified by chromatography or electrophoretic techniques. Recombinant stratum corneum trypsin-like enzymes may also be produced by biotechnological means by the over-expression of the gene in yeast, bacteria, plant or mammalian cells.

Compositions according to the invention may also include an additional enzyme selected from glycosidases, other proteases, lipases or similar lipid modifying enzymes, ceramidases and mixtures thereof. Preferably the composition comprises 0.00001 to 50%, more preferably 0.001 to 20%, even more preferably 0,001 to 0.1% by weight of the composition of the additional enzyme.

Glycosidases, other proteases and lipases for inclusion in the compositions according to the invention may suitably be isolated from animal, plant, fungal or bacterial sources.

Typical glycosidases include neuraminidase, mannosidase, galactosidase, glucosidase, N-acetyl glucosaminidase and N-acetyl galactosaminidase. Preferably these may be isolated from plant sources including almonds, green coffee beans, and spinach, or may be obtained commercially.

Suitable additional proteases include bromelain, papain, chymotrypsin and chymotrypsin-like enzymes, stratum corneum chymotryptic-like enzyme, lysosomal cathepsin and cathepsin-like enzymes, alcalase, savinase, chymopapain, clostripain, endoproteinase Asp N, protease V.8, proteinase K, subtilisin, thermolysin, plasmin, pronase, and trypsin and trypsin-like enzyme. Preferably the protease may be isolated from plant sources including the seeds of wheat, barley, maize, oilseed rape, cocoa, linseed, illipe, shea nut, palm kernal, jojoba bean, pea, green bean, broad bean, soya bean and sunflower, and olives, papaya, pineapple, coconut, tomato and figs.

Lipases, or similar lipid modifying enzymes, may be isolated from plant, animal or bacterial sources. Suitable enzymes include lipolase, pancreatic lipases, phospholipases, ceramidase, aryl sulphatase, cholesterol esterase, candida rugosa OF360 lipase, humicola sp. lipase, pseudomonas sp. lipase and Candida antarctica A and B lipases.

Compositions according to the invention preferably also comprises a vehicle to act as a dilutant, dispersant or carrier for the active ingredients in the composition, so as to facilitate their distribution when the composition is applied to the skin and/or hair. Preferably the vehicle is cosmetically and/or pharmaceutically acceptable.

Vehicles other than water can include liquid or solid emollients, solvents, humectants, thickeners and powders typically found in cosmetic formulations. Examples of each of these types of vehicle, which can be used singly or as mixtures of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmirate, silicone oils such as dimethylpolysiloxane, di-n-butyl sebacate, isopropyl myristate, isopropyl palmirate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitatic acid, isopropyl linoleate, lauryl lactate, myristyl lactate, decyl oleate, myristyl myristate;

Propellants, such as air, propane, butane, isobutane, dimethyl ether, carbon dioxide, nitrous oxide;

Solvents, such as squalene, squalane, ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Humectants, such as polyhydric alcohols including glycerol, polyalkylene glycols and alkylene polyols and their derivatives, including propylene glycol, dipropylene glycol polypropylene glycol, polyethylene glycol and derivatives thereof, sorbitol, hydroxysorbitol, 1,3-butylene glycol, 1,2,6-hexanetriol, ethoxylated glycerol, propoxylated glycerol and mixtures thereof.

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The vehicle will usually form from 10 to 99.9%, preferably from 50 to 99% by weight of the emulsion, and can, in the absence of other adjuncts, form the balance of the composition.

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

Compositions according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

Compositions according to the invention may also optionally comprise one or more emulsifiers the choice of which will normally determine whether a water-in-oil or an oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set out below in Table 1 in which the chemical name of the emulsifiers is given together with an example of a trade name as commercially available, and the average HLB value.

TABLE 1

| Chemical Name of Emulsifier | Trade Name | HLB Value |
| --- | --- | --- |
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate X | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | |
| 12.4 Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene 20 sorbitan monooleate | Tween 80 | 15.0 |

TABLE 1-continued

| Chemical Name of Emulsifier | Trade Name | HLB Value |
|---|---|---|
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 Ms | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

The compositions of the invention can also comprise water, usually up to 80%, preferably from 5 to 80% by volume.

Emulsifiers or surfactants in the form of silicone polymers may be incorporated into compositions of the present invention in place of or in addition to the optional emulsifier(s) already mentioned.

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Various other adjuncts conventionally found in cosmetic or pharmaceutical formulations may optionally be present in the compositions according to the present invention. The include preservatives, such as para-hydroxy benzoate esters; antioxidants, such butyl hydroxy toluene; humectants, such as glycerol, sorbitol, 2-pyrrolidone-5-carboxylate, dibutylphthalate, gelatin, polyethylene glycol, preferably PEG 200–600; buffers, such as lactic acid together with a base such as triethanolamine or sodium hydroxide; surfactants, such as glycerol ethers, waxes, such as beeswax, ozokerite wax, paraffin wax; plant extracts, such as Aloe vera, cornflower, witch hazel, elderflower, cucumber; thickeners; activity enhancers; colourants and perfumes.

Various types of active ingredients may optionally be present in the compositions according to the present invention. These include sunscreens, hydroxy carboxylic acids and ketocarboxylic acids or esters thereof and lipids such as ceramides, pseudoceramides (synthetic ceramide-like structures), polyol fatty acid polyesters, sterols, phospholipids, galactosyldiacylglycerols, glycosphingolipids, fatty acids or esters thereof, and mixtures thereof.

Suitable sunscreens include those materials commonly used to block ultraviolet light and may include inorganic sunscreen materials, such as ultrafine titanium dioxide, or organic sunscreens such as p-aminobenzoic acid and esters thereof, ethylhexyl p-methoxycinnamate, 2-ethoxyethyl p-methoxycinnamate or butylmethoxydibenzoylmethane, and mixtures thereof. It will be appreciated that the amount of sunscreen employed will vary depending on the degree of protection required.

Suitable ceramides and synthetic analogues thereof which may be employed are disclosed in European patent application EP-A-587288 which is incorporated by reference herein. Preferred ceramides have the structure.

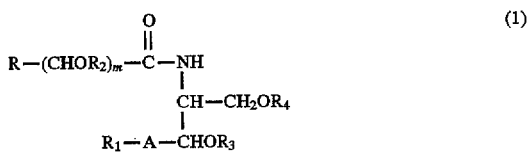

(1)

where A represents $-CH_2-$; $-CHOR_5-$; $-CH=CH-$ or $-CHOY-$

R represents a linear or branched saturated or unsaturated, hydroxylated or non-hydroxylated aliphatic hydrocarbon group having from 1 to 49 carbon atoms or a subgroup (2).

(2)

$R_1$ represents a linear or branched, saturated or unsaturated, hydroxylated or non-hydroxylated aliphatic hydrocarbon group having from 8 to 28 carbon atoms;

$R_2$, $R_3$ and $R_5$ individually represent H, a phosphate residue or a sulphate residue;

$R_4$ represents H, a phosphate residue, a sulphate residue or sugar residue;

a is an integer of from 1 to 49 b is an integer of from 10 to 98 m is 0 or 1

Y represents H or a residue of a $C_{1-22}$ fatty acid having the general structure (3)

(3)

where

Z is —OH or an epoxy oxygen x is an integer of from 0 to 20 y is an integer of from 0 to 40 and z is 0 or an integer of from 1 to 4

Ceramides having the general structure (1) are naturally occurring and can be isolated from a suitable plant source or from animal tissue such as pig skin or neural tissue. Ceramides can also be synthesised.

Particular preferred examples of ceramides are ceramide-1, ceramide-2 and ceramide-3.

Pseudoceramides are preferably selected from pseudoceramides (i.e. synthetic ceramide like structures) having the general structure (4):

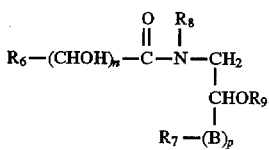

where B represents —OCH$_2$— or CHOH.

R$_6$ represents a linear or branched, saturated or unsaturated, hydroxylated or non-hydroxylated aliphatic hydrocarbon group having from 1 to 49 carbon atoms or the subgroup (2).

R$_7$ represents a linear or branched, saturated or unsaturated, hydroxylated or non-hydroxylated hydrocarbon group having from 8 to 28 carbon atoms.

R$_8$ represents H, or a subgroup —(CH$_2$)$_c$COOH, where c is an integer of from 1 to 6, or a subgroup having the structure (5).

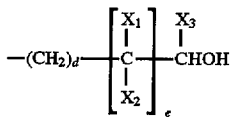

where X$_1$, X$_2$ and X$_3$ each individually represent H, a C$_{1-5}$ alkyl or a C$_{1-5}$ hydroxyalkyl;

d is 0 or an integer of from 1 to 4 e is 0 or 1 n is 0 or 1 and p is 0 or 1;

R$_9$ represents H, a phosphate residue, a sulphate residue or a sugar residue.

Polyol fatty acid polyesters are fatty acid polyesters derived from any aliphatic or aromatic polyol which has at least 4 free hydroxyl groups, of which at least 60% of these free hydroxyl groups are then esterified with one or more fatty acids having from 8 to 22 carbon atoms. The polyol from which the polyol fatty acid polyesters are derived are preferably chosen from sugar polyols, which comprise mono-, di- and polysaccharides.

Particularly preferred polyol fatty acid polyesters are sucrose fatty acid polyesters where the ester is derived from lauric acid or natural oils, such as palm oil, palm kernal oil, soyabean oil, coconut oil, fish oil and mixtures thereof.

Preferably the amount of the lipid component where present in the composition according to the invention is from 0.00001 to 50%, more preferably from 0.001 to 20% and most preferably from 0.1 to 10% by weight of the composition.

Compositions according to the invention may also suitably comprise hydroxy carboxylic acids and keto carboxylic acids, esters thereof and mixtures thereof.

The hydroxy acid can be chosen from α-hydroxy acids, β-hydroxyacids, other hydroxycarboxylic acids and mixtures thereof.

Preferably the hydroxy acid (ii) is chosen from α-hydroxy acids having the general structure:

R$_b$CHOHCOOR$_a$ wherein R$_a$ and R$_b$ are H, alkyl, aralkyl or aryl group of saturated or unsaturated, isomeric or non-isomeric, straight or branched chain or cyclic form, having 1 to 30 carbon atoms, and in addition R$_2$ may carry F, Cl, Br, I, N, S, OH, CHO, COOH and alkoxy group having 1 to 9 carbon atoms; and mixtures thereof.

The alpha hydroxy acids may be present as a free acid or an ester form, or in a salt form with an organic base or an inorganic alkali. The typical alkyl, aralkyl and aryl groups for R$_1$ and R$_2$ include methyl, ethyl, propyl, isopropyl, butyl, pentyl, octyl, lauryl, stearyl, benzyl and phenyl, etc.

D, DL, or L stereoisomeric forms of an alpha hydroxy acid may be employed in compositions. The L form is preferred.

Suitable alpha hydroxy acids which may be used include, but are not limited to, alpha hydroxy acetic acid (also known as "glycolic acid") , alpha hydroxypropionic acid (also known as "lactic acid"), alpha hydroxyoctanoic acid (also known as "alpha hydroxy caprylic acid"), alpha hydroxydodecanoic acid (also known as "alpha hydroxy lauric acid") and mixtures thereof.

Suitable esters include, but are not limited to, alkyl esters (for example, methyl, ethyl, propyl, pentyl, hexyl, octyl esters) and mono-, di- or triglycerides, or mixtures thereof.

Suitable salts of alpha hydroxy acids include but are not limited to sodium, potassium, ammonium, triethanolamine, calcium, lithium salts. The salts may be obtained commercially or they may be prepared by methods known in the art, e.g., neutralizing an alpha hydroxy acid with a suitable base, such as hydroxide bases of ammonium, potassium, sodium.

Conveniently, a mixture of alpha hydroxy acids may be employed. A suitable mixture comprises lactic acid, alpha hydroxy octanoic acid and alpha hydroxy lauric acid.

The preferred compositions according to the invention contain at least 60% of an alpha hydroxy acid in L-configuration, by weight of total alpha hydroxy acid.

The alpha hydroxy acid is suitably present in an amount of from 0.001% to 70%, preferably from 0.1% to 20%, most preferably from 1% to 10% by weight of the composition.

The keto acids can be chosen from α-keto acids, β-keto acids and mixtures thereof. A particularly preferred α-keto acid is 2-keto octanoic acid.

Preferably the amount of the organic acid component where present in the composition according to the invention is from 0.01 to 20%, more preferably from 0.05 to 10% and most preferably from 0.1 to 2% by weight.

Sterols may conveniently be selected from cholesterol, pro-vitamin D$_3$, campesterol, stigmastanol, stigmasterol, 5-dihydrocholesterol, α-spinasterol, palysterol, clionasterol, γ-sitosterol, stigmastenol, sargasterol, avenasterol, ergostanol, sitosterol, corbisterol, chondrillasterol, poriferasterol, haliclonaseterol, neospongosterol, fucosterol, aptostanol, Ergostadienol, ergosterol, 22-dihydroergosterol, brassicasterol, 24-methylenecholesterol, 5-dihydroergosterol, dehydroergosterol, 14-dehydroergosterol, 24-dehydroergosterol, fungisterol, cholestanol, coprostanol, Zymosterol, 7-herocholesterol, Lathosterol, 22-dehydrocholesterol, 6-sitosterol, cholestatrien-36-01, coprostanol, cholestanol, ergosterol, 7-dehydrocholesterol, 24-dehydrocholest-adione-36-01, equilenin, equilin, estrone, 176-estradiol, Androst-4-ene-36, 176-diol, dehydroepiandrosterone and mixtures thereof. Cholesterol is preferred.

The fatty acids are preferably essential fatty acids chosen from linoleic acid, γ-linolenic acid, homo-γ-linolenic acid, columbinic acid, eicosa-(n-6,9,13)-trienoic acid, arachidonic acid, α-linolenic acid, timnodonic acid, hexaenoic acid and mixtures thereof.

Non-essential fatty acids can also be employed in addition to or in place of essential fatty acids, examples of which are chosen from myristic, palmitic, stearic and isostearic acids, and mixtures thereof.

Compositions according to the invention may also include chelating agents, particularly those having high affinity with zinc and/or magnesium ions.

Suitable chelating agents may conveniently be selected from aminocarboxylic acids or salts thereof, polyphosphoric acids or salts thereof, diphosphonic acids, salts of diphosphonic acids, tertiary amines, aminophosphonic acids, iminodiacetic acid derivatives, azines, hydroxyquinolines, and amino acid esters.

Examples of suitable chelating agents include but are not limited to ethylene diamine tetraacetic acid, a salt of ethylene diamine tetraacetic acid, sodium pyrophosphate, sodium tripolyphosphate, 8-hydroxyquinoline, DL-(Methylene) dinitrolo tetra acetic acids, trans-decahydronaphthylene-trans-2, 3-bis-iminodiacetic, aminophenyl methylene diphosphonic acid, ethylene-bis-N,N1-(2,6-carboxyl) piperdine, adenosine triphosphate, L-cysteine methyl ester and 8-hydroxyquinoline.

Preferred chelating agents are EDTA and/or pyrophosphate, and/or 8-hydroxyquinoline due to their ready availability, excellent performance, relatively low cost, and safety in use.

The chelating agent is employed in the inventive compositions in an amount effective to enhance the activity of the enzyme. It will be appreciated that the precise amount will depend on the particular chelating agent used. Typically, the amount is in the range of 0.1 to 2%, preferably from 0.2 to 2% by weight of the composition.

Compositions according to the invention are useful in treating or alleviating conditions of the skin which are characterised by hyperkeratinisation, decreased rate of desquamation or abnormal desmosomal formation.

Accordingly, the invention provides the cosmetic or pharmaceutical use of a composition comprising one or more stratum corneum trypsin-like enzymes, particularly in the treatment of conditions where the underlying aetiology indicates that assisting desquamation and/or desmosomal degradation would be beneficial.

The invention further provides a method of treating skin comprising topically administering thereto a composition comprising one or more stratum corneum trypsin-like enzymes.

It will be appreciated that compositions according to the invention will primarily be of use in the treatment of established symptoms although prophylaxis is not excluded.

Compositions according to the invention are of use in treating or preventing diseases of the skin such as psoriasis, ichthyosis and acne. Compositions according to the invention are of particular interest in treating dry and/or flaky skin and in smoothing and enhancing the quality of skin. The compositions may also be used to alleviate dandruff.

It will be appreciated that the amount of the composition and the frequency of its application to the skin will depend on the condition of the patient.

In use, a small quantity of the composition, for example from 1 to 5 ml, is applied to areas of the skin or scalp, from a suitable container or applicator and, if necessary, it is then spread over and/or rubbed into the skin or scalp using the hand or fingers or a suitable device.

The topical skin treatment compositions according to the invention may be formulated in conventional manner using one or more cosmetically and/or pharmaceutically acceptable carriers or excipients.

For example, the topical compositions of the invention may suitably be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The composition may be used for general lotions and creams, leave-on-creams, wash-off cleansers, face masks shampoos and bath oils.

The invention accordingly also provides a closed container containing an acceptable composition as herein defined.

CHARACTERISATION OF STRATUM CORNEUM TRYPSIN-LIKE ENZYMES

1) Superose 12 fractionation

Stratum corneum trypsin-like activity was derived from either human tape stripped or freeze scraped pig stratum corneum. The tissues were extracted in 1M sodium chloride in 0.05M sodium acetate pH6, 0.1% (v/v) Triton X-100 at 4° C. and the extracts were fractionated using a Superose 12 gel filtration column (Pharmacia) with a buffer of 0.02M sodium acetate pH6 containing 1M sodium chloride.

The column was calibrated using standard proteins, namely haemoglobin (68 KDa), carbonic anhydrase (29 KDa), bovine chymotrypsin (25 KDa) and cytochrome c (14 KDa). The void volume was determined using dextran blue and the bed volume using $CuSO_4$. Stratum corneum trypsin-like enzyme detected by boc-phe-ser-arg-AMC hydrolysis had an apparent molecular weight of 29 KDa on this system (FIG. 1).

2) Cation Exchange Chromotography

Figure 2:
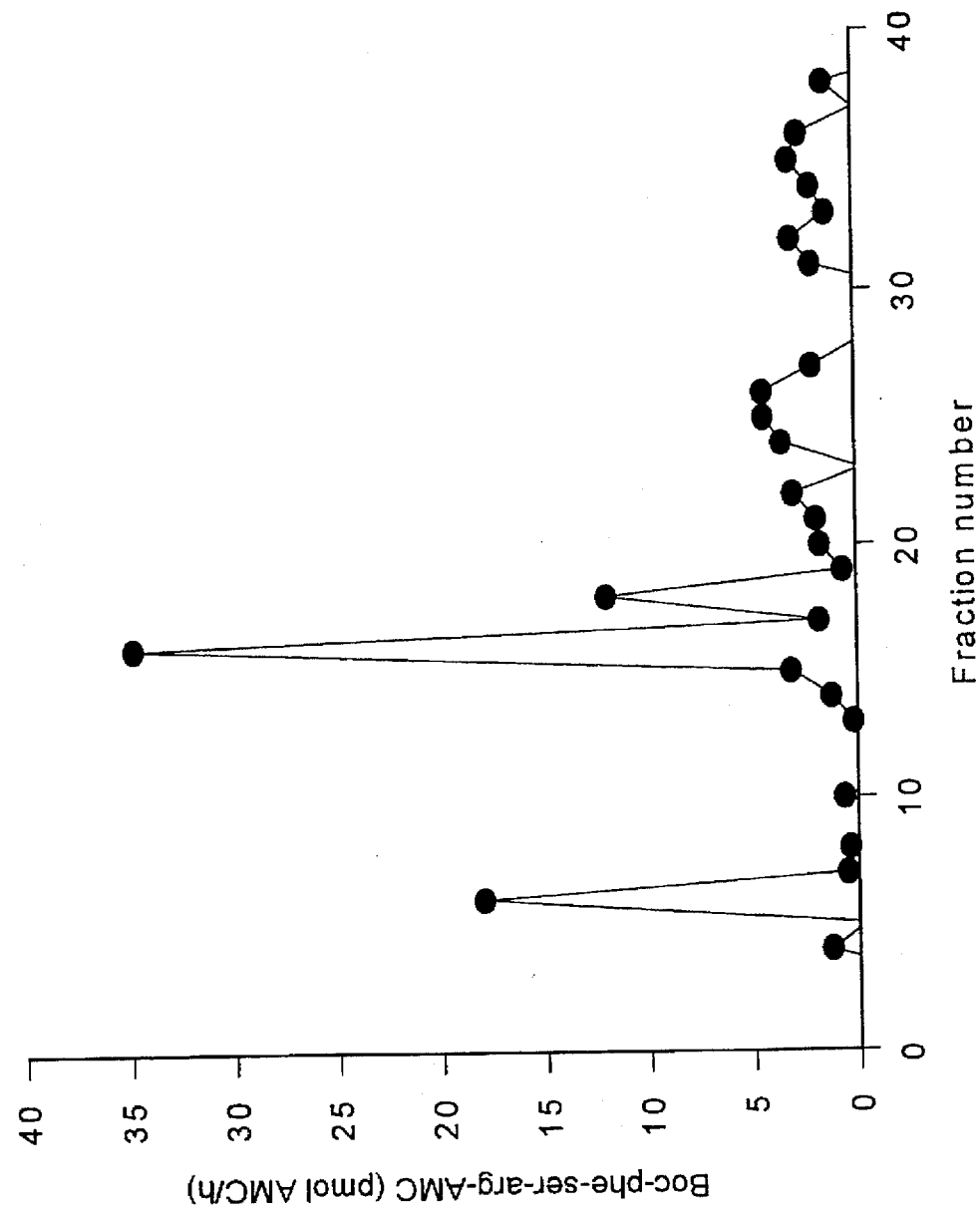
FIG. 2 depicts a cation exchange chromatography profile of 29 kDa fraction (having boc-phe-ser-arg-AMC activity).

Further purification was achieved using cation exchange chromatography with a Mono S column (Pharmacia). The 29 kDa fraction from the Superose 12 column was desalted, loaded onto the Mono S column in 0.02M ammonium acetate pH5 and eluted with a gradient of 1M sodium chloride over 30 fractions (FIG. 2) and was started at fraction 11.

Activity was determined using the fluorescent proteolytic substrate boc-phe-ser-arg-amido-methylcoumarin by incubating in 50mM tris-HCl pH7.5, 0.1% (v/v) Triton X100, 0.1% (w/v) sodium azide containing 100 μM boc-phe-ser-arg-amido-methylcoumarin and incubated at 37° C. for 3 h. Termination of the reaction was by addition of 250 μl of 100 mM sodium monochloroacetic acid, 30 mM sodium acetate, 70 mM acetic acid, pH4.3 and proteolytic activity was determined using a Perkin Elmer LS50 fluorescence spectrophotometer with emission at 380 nm and detection at 460 nm.

Caseinolysis was determined using casein zymography by a modification of Horie et al, "Detection and characterisation of epidermal proteinases by polyacrylamide gel electrophoresis", Comp. Biochem. Physiol 77B, 349–353 (1984). The samples were fractionated by sodium dodecyl sulphate (SDS) polyacrylamide gel electrophoresis using 12% gels containing 0.2% (w/v) casein. After fractionation, the gels were washed to remove SDS and incubated in 0.1M tris pH8 for 24 h. The reaction was stopped by staining with coomassie blue in 10% acetic acid and 40% methanol. Caseinolysis was determined from densitometric analysis of the clear band produced by the protease.

Only one fraction contained both boc-phe-ser-arg-AMC hydrolytic and caseinolytic activities, indicating stratum corneum trypsin-like activity.

3) Inhibition Profile

An inhibition profile for the stratum corneum trypsin-like enzyme was produced using specific protease inhibitors.

Figure 3:
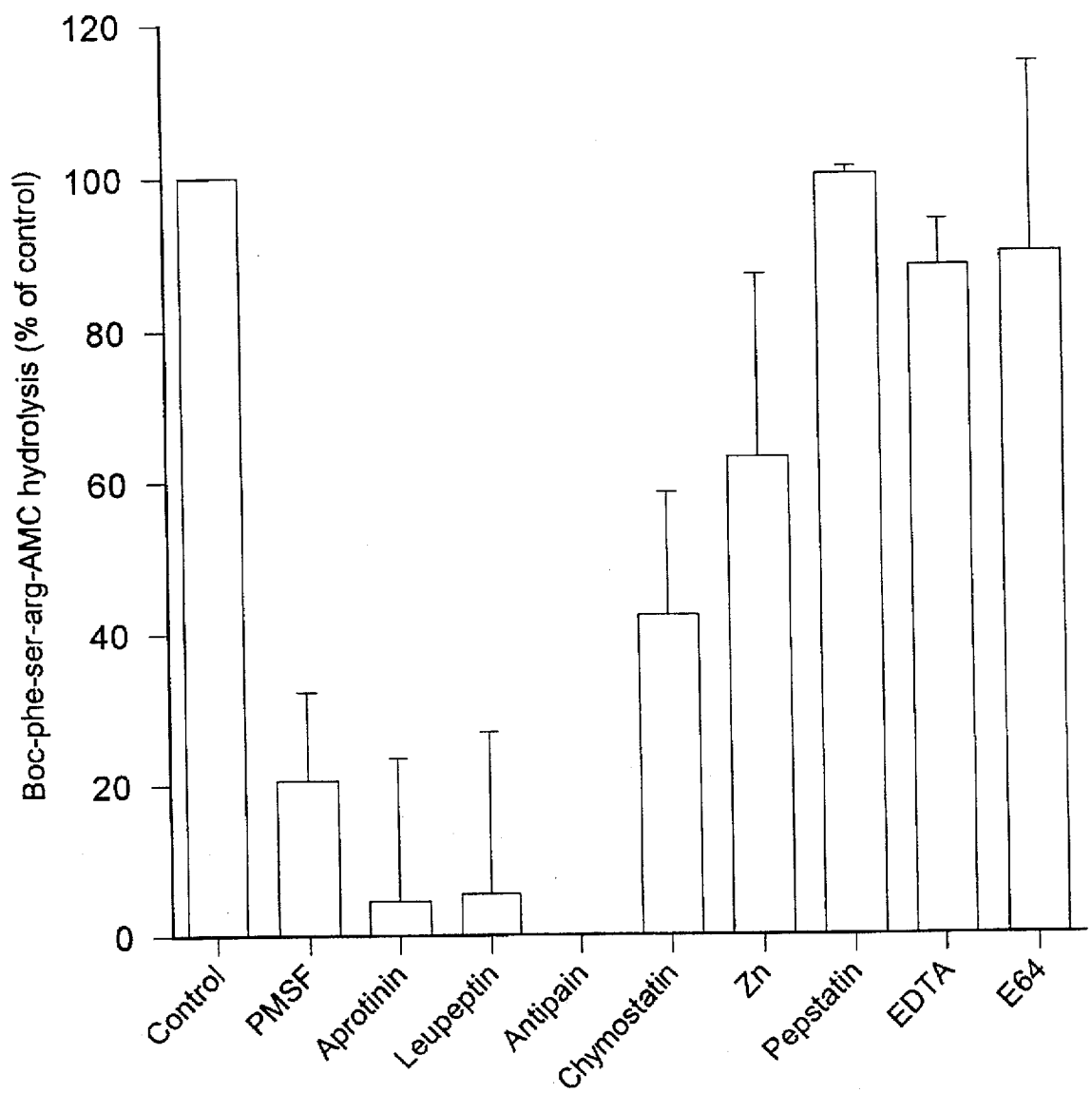
FIG. 3 depicts an inhibition profile of stratum corneum 29 kDa trypsin-like enzyme.

Boc-phe-ser-arg-AMC hydrolyric activity was determined and expressed as a percentage of the control value (FIG. 3). The concentrations of inhibitors used were 2 mM PMSF, 1 µM aprotinin, 100 µM leupeptin, 100 µM antipain, 100 µM chymostatin, 100 µM zinc sulphate, 1 µM pepstatin and 1 µM E64.

Trypsin specificity was shown by the inhibition of boc-phe-ser-arg-AMC hydrolyric activity in the presence of the trypsin inhibitors leupeptin and antipain.

4) Effect on Desmosomal Degradation

Human sunburn peeled stratum corneum was incubated with stratum corneum trypsin-like enzyme (boc-phe-ser-arg-AMC hydrolysis equivalent to 17 pmol AMC/h) for 20 h in 0.1M tris pH8, 0.1% (w/v) sodium azide at 37° C.

After incubation, the skin was washed in tris buffered saline containing 0.5% (v/v) Tween 20 and incubated for 1 h at 37° C. with a desmosomal marker antibody (α48/46) raised against the 46 and 48 kDa N-terminal fragments of human desmocollin 1 (dsc 1) (Gift from Dr I King, N. I. M. R). This was followed by incubating for 1 h with an anti-rabbit IgG conjugated to FITC and the resulting fluorescence was detected by microscopy with a U.V. light source. The fluorescence was quantified from photographic negatives using an Epson GT8000 scanner coupled with Phoreti image analysis software.

Figure 4:
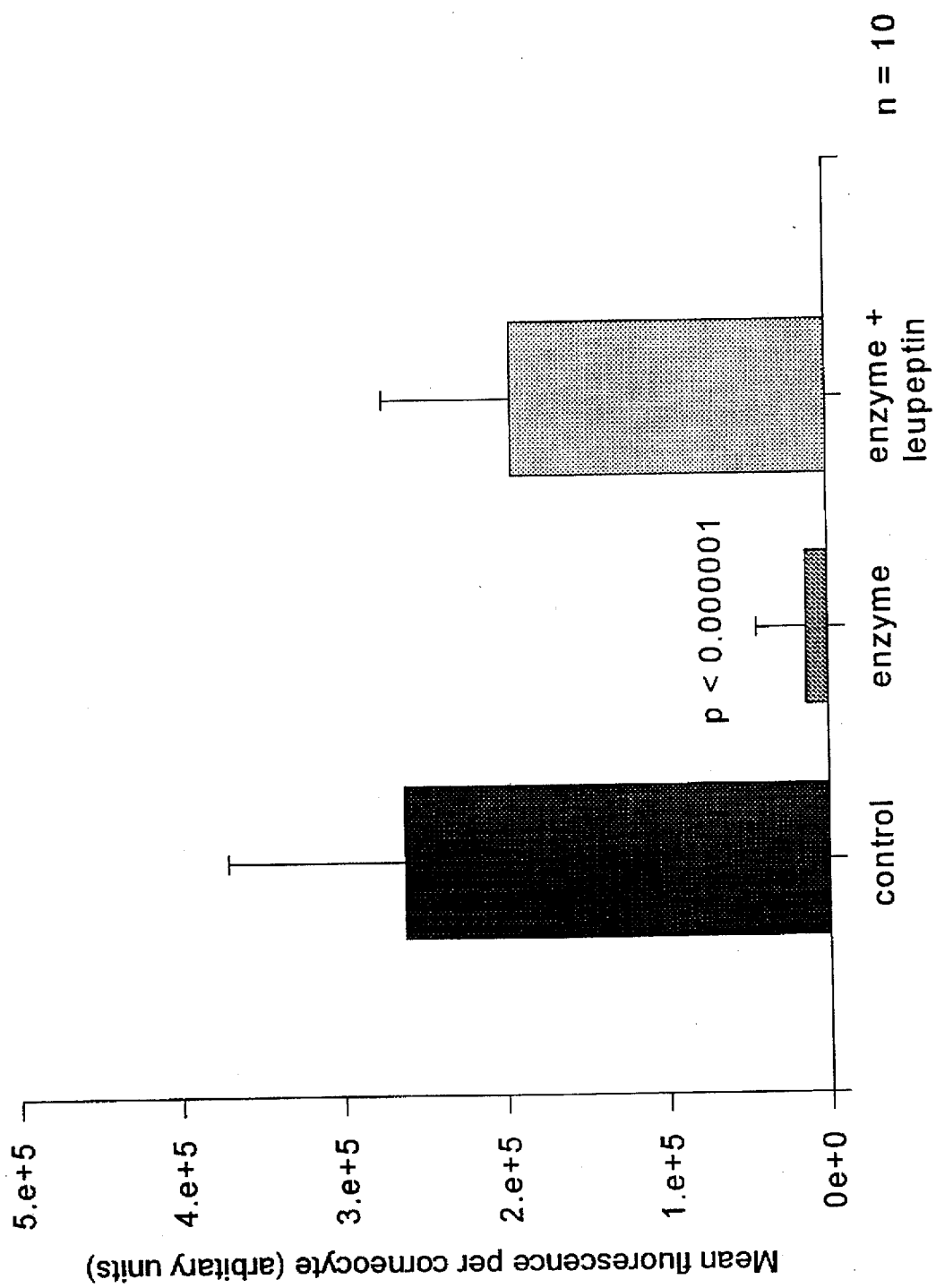
FIG. 4 depicts an effect of stratum corneum trypsin-like enzyme on desquamation.

The results obtained are presented graphically in FIG. 4. The levels of dsc1 are significantly decreased by stratum corneum trypsin-like enzyme, indicating desmosomal degradation. This degradation was inhibited by leupetin (100 µM), a trypsin specific inhibitor.

5) The gel filtration purified 29 kDa peak of boc-phe-ser-arg-AMC hydrolytic activity contained the trypsin-like caseinolytic proteases with 24, 26 and 27kDa apparent molecular weights. Using casein zymography, the inhibitor profiles of these proteases were determined.

Trypsin specificity was shown by the inhibition of caseinolysis in the presence of 100 µM antipain, leupeptin and TLCK.

|  | % inhib | sd | n |
|---|---|---|---|
| Apparent molecular weight 27 KDa | | | |
| PMSF | 68.7 | 22.0 | 4 |
| Aprotinin | 85.4 | 11.5 | 4 |
| Chymostatin | 82.6 | 15.1 | 3 |
| Leupeptin | 77.8 | 16.8 | 4 |
| Antipain | 68.7 | 26.8 | 4 |
| TPCK | 70.0 | 25.9 | 3 |
| TLCK | 70.8 | 7.6 | 3 |
| Apparent molecular weight 26 KDa | | | |
| PMSF | 61.0 | 24.3 | 3 |
| Aprotinin | 97.1 | 2.5 | 4 |
| Chymostatin | 70.02 | 20.3 | 3 |
| Leupeptin | 75.6 | 19.5 | 4 |
| Antipain | 70.7 | 20.4 | 4 |
| TPCK | 58.6 | 32.6 | 3 |
| TLCK | 65.4 | 15.2 | 4 |
| Apparent molecular weight 24 KDa | | | |
| PMSF | 77.6 | 19.05 | 3 |
| Aprotinin | 95.5 | 6.36 | 4 |
| Chymostatin | 70.4 | 28.13 | 4 |
| Leupeptin | 50.6 | 55.87 | 4 |
| Antipain | 24.0 | 65.11 | 3 |
| TPCK | 73.5 | 15.50 | 4 |
| TLCK | 53.6 | 12.31 | 4 | sd = standard deviation
n = number of samples

In order that the invention may be well understood, the following examples are given by way of illustration only.

EXAMPLES

The following examples are to illustrate compositions for topical application embodying the present invention.

|  | % w/w |
|---|---|
| A Typical Oil-In-Water Cream | |
| SCTE | 1.0 |
| Glycosidases | 0.5 |
| Mineral oil | 4.0 |
| Cetyl alcohol POE | 4.0 |
| Cetyl alcohol | 4.0 |
| Triethanolamine | 0.75 |
| Butane 1,3 diol | 3.0 |
| Xanthum gum | 0.3 |
| Preservative | 0.4 |
| Perfume | qs |
| Butylated hydroxytoluene | 0.01 |
| Water | to 100 |
| A Typical Lotion | |
| SCTE | 1.0 |
| Ethanol | 10.0 |
| Perfume | qs |
| Butylated hydroxytoluene | 0.01 |
| Water | to 100 |

We claim:

1. A method of relieving or ameliorating dry skin, acne and for smoothening skin which by topical application to the skin of a composition consisting essentially of a stratum corneum serine protease which in its active form is inhibited by antipain and leupeptin and is capable of decomposing the substrate boc-phe-ser-arg-aminomethylcoumarin.

2. A method according to claim 1 wherein the stratum corneum serine protease has an apparent molecular weight of 26 kDa when determined by sodium dodecyl sulphate polyacrylamide gel.

3. A method according to claim 1 wherein the stratum corneum serine protease has an apparent molecular weight of 27 kDa when determined by sodium dodecyl sulphate polyacrylamide gel.

4. A method according to claim 1 wherein the stratum corneum serine protease has an apparent molecular weight of 24 KDa when determined by sodium dodecyl sulphate polyacrylamide gel electrophoresis.

5. A method according to claim 1 wherein the stratum corneum serine protease is present in an amount of from 0.001 to 20% by weight of the composition.

6. A method of relieving or ameliorating dry skin, acne and for smoothening skin by topical application to the skin of a composition consisting essentially of:

a) a stratum corneum serine protease which in its active form is inhibited by antipain and leupeptin and is capable of decomposing the substrate boc-phe-ser-arg-aminomethylcoumarin; and b) a protease selected from the group consisting of bromelain, papain, chymotrypsin, lysosomal, cathepsin, alcalase, savinase, chymopapain, clostripain, endoproteinase Asp N, protease V.8, proteinase K, subtilisin, thermolysin, plasmin, pronase, and trypsin.

7. A method of relieving or ameliorating dry skin, acne and for smoothening skin by topical application to the skin of a composition consisting essentially of:

(a) a stratum corneum serine protease which in its active form is inhibited by antipain and leupeptin and is capable of decomposing the substrate boc-phe-ser-arg-aminomethylcoumarin; and (b) an enzyme selected from glycosidases, lipases and mixtures thereof.

* * * * *